United States Patent [19]

Phillips

[11] Patent Number: 4,606,077
[45] Date of Patent: Aug. 19, 1986

[54] SUN VISOR

[76] Inventor: Robert F. Phillips, P.O. Drawer 811, Spartanburg, S.C. 29304

[21] Appl. No.: 729,235

[22] Filed: May 1, 1985

[51] Int. Cl.4 .............................................. A61F 9/00
[52] U.S. Cl. ........................................... 2/012; 2/195; 2/200
[58] Field of Search ...................... 2/195, 12, 200, 197, 2/DIG. 11, 411, 192

[56] References Cited

U.S. PATENT DOCUMENTS

| | | | |
|---|---|---|---|
| 1,404,616 | 1/1922 | Kronthal | 2/197 |
| 1,506,815 | 9/1924 | Cormay | 2/195 |
| 1,816,346 | 7/1931 | Silverstein | 2/195 |
| 1,818,765 | 8/1931 | Silverstein | 2/195 |
| 2,718,010 | 9/1955 | Graham | 2/195 |
| 2,875,447 | 3/1959 | Goldmerstein | 2/195 |
| 2,883,669 | 4/1959 | Rafowitz | 2/195 |
| 3,344,437 | 10/1967 | Greene | 2/195 |
| 3,445,860 | 5/1969 | Rodell | 2/195 |
| 4,133,055 | 1/1979 | Zebuhr | 2/411 |
| 4,293,958 | 10/1981 | Zauner | 2/209.1 |
| 4,356,048 | 10/1982 | Price | 2/195 |
| 4,443,891 | 4/1984 | Blomgren | 2/192 |

Primary Examiner—Henry S. Jaudon
Assistant Examiner—Mary A. Ellis
Attorney, Agent, or Firm—Dority & Manning

[57] ABSTRACT

A washable, reversible sun visor including a head encircling adjustable body section with a bill section secured to a front portion of same and extending downwardly and outwardly therefrom. The body section includes a base material, preferably an open cell foam with outer and inner covering materials secured thereabout and an adjustment means, preferably an elastic strip. The bill section includes a flexible polymeric bill element with upper and lower covering materials secured thereabout. Preferably the bill element defines a plurality of openings thereacross through which water may drain.

13 Claims, 5 Drawing Figures

U.S. Patent  Aug. 19, 1986  4,606,077
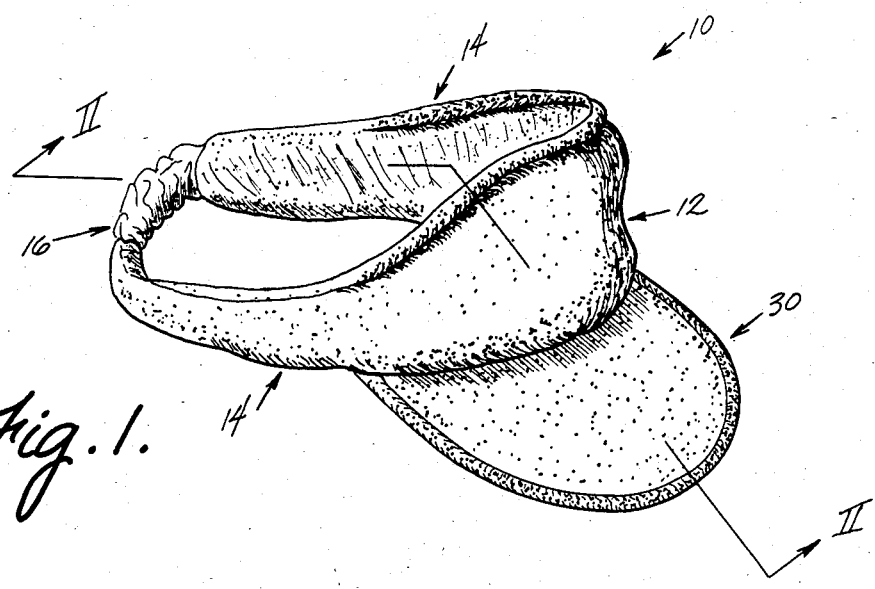
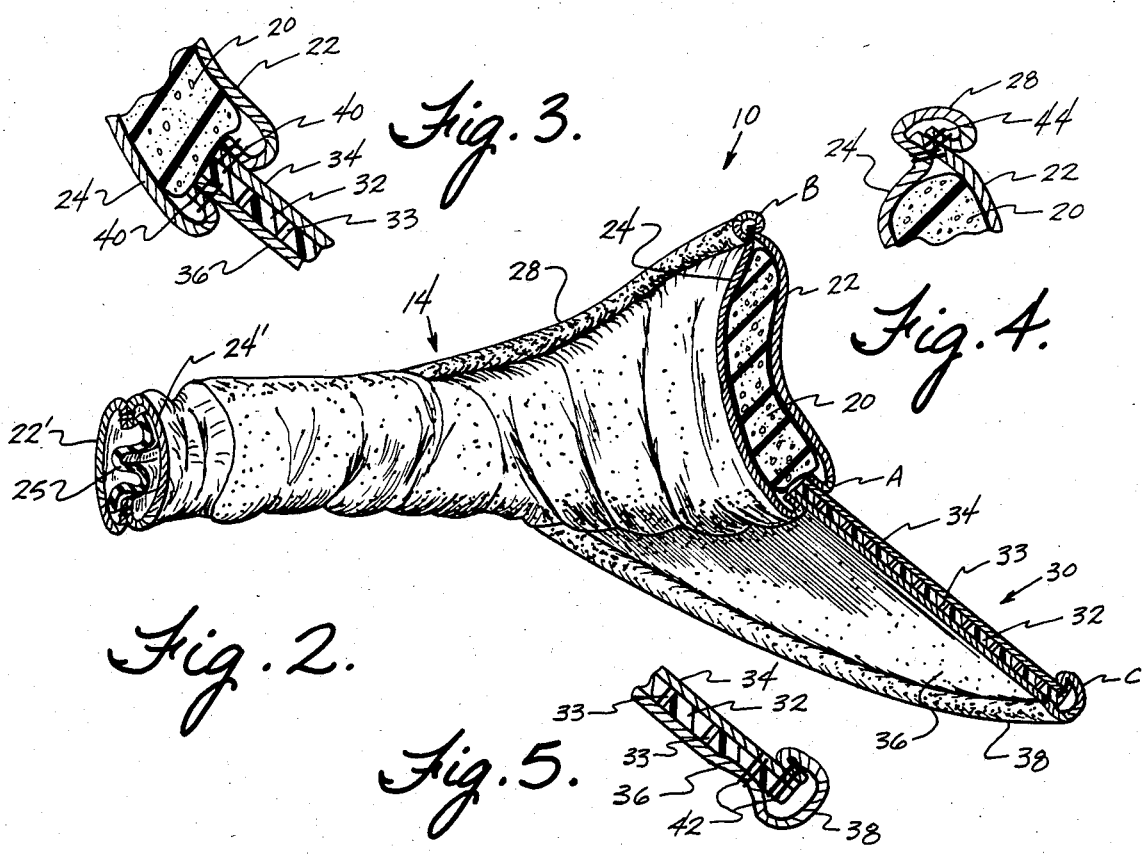

SUN VISOR

BACKGROUND OF THE INVENTION

The present invention relates to a sun visor of the type that is normally worn by one participating in or observing a sporting event, at the seacoast, or the like.

Sun visors of the general type to which the present invention relates have heretofore been available in various and sundry forms in which a band of material or element is received about the head of the wearer leaving the top of the head uncovered, and having some means for size adjustment generally at a rear portion of same. A visor or bill is secured to a front of the head band and extends outwardly and downwardly therefrom to shade the eyes and a portion of the face from the sun. Conventionally, such sun visors have been low-cost items, intended for sporadic or one-time use, and are generally considered to be disposable. Due in part to the general low-cost requirements for same, cardboard or other type paper sheet material has been utilized as a stiffening material in both the headband and bill portions of the sun visor with interchangeable polymeric strips or other type adjustment means located at the rear of same. Furthermore, outer coverings about the stiffening materials have conventionally been tricot or terry type fabrics or the like. Sun visors of the type described above are intended for use only as originally presented, i.e. are not reversible, and due to utilization of cardboard, paper or other similar type stiffening materials, may not be exposed to water without destruction of integrity of the materials.

The improved sun visor according to teachings of the present invention is extremely more versatile than known prior art visors, in that, it is reversible, washable, and may in fact, as a further benefit, receive a hold a cooling medium about the head of the wearer.

In addition to the general visors as described above, other known prior art includes the following U.S. Pat. Nos. 757,854; 3,266,056; 1,484,042; 2,626,869; 2,019,028; 4,258,437; 4,293,958; 2,003,367; 1,213,447; 1,563,611; 4,393,519; 2,859,448 and 4,277,847. The sun visor of the present invention is neither anticipated nor obvious in view of the known prior art.

SUMMARY OF THE INVENTION

It is an object of the present invention to provide an improved sun visor.

Another object of the present invention is to provide an improved sun visor that is reversible in nature.

Still another object of the present invention is to provide an improved, washable sun visor.

Still further another object of the present invention is to provide an improved sun visor adapted to be received about the human head, is adjustable as to size, is reversible, and washable.

Still further, another object of the present invention is to provide an improved sun visor that is capable of supplying a cooling medium to the head of one wearing same.

Generally speaking, the sun visor of the present invention comprises a generally circular flexible body section for receipt about a human head, said body section having front, side and rear portions, said body section having a base material along at least a major portion of the circumference of same and adjustment means located along at least one of said side and rear portions, said body section having an outer covering material and an inner covering material, said covering materials being secured about said base material, and a flexible bill element secured to said body section along a lower edge of said front portion of same to form a generally convex curvature, said bill element being inert as to water and having top and bottom covering materials secured thereabout, said bill element and said body section being associated to achieve reversibility where said inner covering material of said body section becomes the outer covering and said bottom covering material of said bill element becomes the top covering.

More specifically, the improved sun visor of the present invention includes a head encircling body section which utilizes a base material that is a polymeric foam or sponge element, preferably an open celled polymeric foam or sponge, provided along at least a major portion of the circumference of the body section with the remainder of the body section being provided by the adjustment means, preferably an elastic strip that is secured between opposite ends of the base material. Outer and inner covering materials, which in a most preferred arrangement are an absorbent fabric such as a terry-type fabric, are secured about the body section for both functional and decorative purposes. Particularly, the covering material on the outside affords a decorative affect to the sun visor while the covering material on the inside, being absorbent in nature may absorb perspiration or transmit a cooling medium from the base material to the head of the wearer. The covering material may or may not be secured about the adjustment means, depending upon the desired intended overall appearance of the sun visor and the type of adjustment means employed. A polymeric bill element is secured to a lower front portion of the body section and extends outwardly and downwardly therefrom. With the bill element being secured about a portion of an arc of the body section, in the attached configuration, an upper surface of the bill element assumes a generally convex or rounded curvature. The bill element likewise is provided with top and bottom covering materials, preferably fabrics of the type employed on the body section. In a most preferred embodiment, the polymeric bill section further defines a plurality of openings thereacross which permit water drainage therethrough.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein:

FIG. 1 is a generally isometric view of a sun visor according to teachings of the present invention.

FIG. 2 is a vertical cross-sectional view through the sun visor as shown in FIG. 1 taken along a line generally indicated as II—II.

FIG. 3 is an enlarged vertical cross-sectional view taken along line II—II at the juncture between the bill element and the body section of the visor as indicated as A in FIG. 2.

FIG. 4 is a enlarged vertical cross-sectional view taken along line II—II, of a portion of the body section of the visor taken as indicated generally at point B in FIG. 2.

FIG. 5 is an enlarged vertical cross-sectional view taken along line II—II of a portion of the bill element as indicated and generally at point C in FIG. 2.

DESCRIPTION OF THE PREFERRED EMBODIMENT

Making reference to the figures, preferred embodiments of the present invention will now be described in detail.

As illustrated in FIGS. 1 and 2, the sun visor of the present invention includes a head encircling body section generally indicated as 10 and a bill section generally indicated as 30 secured to body section 10. Body section 10 has a front portion generally 12, side portions generally 14, and a rear portion 16 which are united to form the circumference of the head encircling body section 10. Body section 10 includes a base material, preferably an open-celled foam or sponge 20 that extends around at least a major portion of the circumference of body section 10, and preferably around at least front portion 12 and side portions 14. As used herein, the term open celled foam or spong refers to a synthetic or natural material in which a series of interconnecting cells are located throughout the material. An adjustment means 25 is provided along at least one of side portions 14 and rear portion 16. As illustrated in FIG. 2, adjustment means 25 is an elastic strip secured along rear body portion 16. Any other conventional adjustment means may be employed, however, if desired.

Body section 10 further includes an outer covering material 22 and an inner covering material 24 which are secured about the foam base material 20 of body section 10. Further in this regard, it is noted that an outer covering of material 22' and an inner covering material 24' are also secured about adjustment means 25. In the form shown, covering material 22, 24, 22' and 24' may constitute one or more independent pieces of material, depending upon the sewing techniques for producing the sun visor, the intended decorative appearance of the sun visor and the like. Particularly, in a preferred embodiment of the present invention, outer covering materials 22 and 22' are of the same color and texture though separate pieces of material while inner covering materials 24, 24' are a different color than the outer covering materials though preferably of a same texture and likewise as illustrated are separate pieces of materials.

Bill section 30 as illustrated in the figures, is secured to body section 10 and includes a flexible polymeric bill element 32 having upper and lower covering materials 34, 36, respectively, secured thereabout. As illustrated particularly in FIG. 3, bill element 32, upper covering 34 and lower covering 36 therefor are all secured to body section 10 by having outer covering material 22 and inner covering material 24 secured thereto by stitches 40. Making particular reference to FIGS. 1, 2, and 3 therefore, it can be seen that the bill section 30 is secured to the outer and inner covering materials 22, 24 along the length of bill element 32. When so secured, bill section 30 assumes a generally convex or arcuate curvature across the top of same, and extends outwardly and downwardly from body section 10.

As particularly illustrated in FIG. 5, bill section 30 may be provided with a bead 38 around the outer periphery of same, formed by bringing lower covering material 36 around the outer peripheral edge of bill element 32 and securing same atop a terminal portion of upper covering material 34 with stitches 42. In like fashion, a similar bead 28 may be provided about an upper portion of body section 10 as illustrated in the figures. With particular reference to FIG. 4, it may be seen that bead 28 may be formed by bringing one of covering materials 22 or 24 over the top of base material 20 and turning same under where it is stitched to the opposite covering material 22 or 24 as by stitches 44.

With the structure of a sun visor as described above, same is more permanent and more versatile than those heretofore available. Particularly, as noted hereinbefore, the outer and inner covering materials 22 and 24 of body section 10 as well as the upper and lower covering materials 32, 36 of bill section 30 may be provided in contrasting, coordinated or otherwise differently colored materials. The materials are prefereably fabrics, and most preferably terry-type fabrics which are provided with a plurality of loops across the surface of same and possess good absorbency characteristics. With the terry-type fabrics utilized as the covering materials, perspiration of one wearing same in the sun or hot weather will be absorbed thereby. Likewise, as noted above, the preferred base material 20 for body section 10 is an open-cell foam or sponge. When such a base material is utilized, water or other liquid may be poured onto body section 10 and will pass through the covering materials to be absorbed by the base material. Thereafter the liquid will exude from the base material, maintaining the head of the wearer moist and cool.

Also, with the sun visor structure as described above, all elements of same are intended to, and do resist deterioration in the presence of water. As such, the sun visor according to teachings of the present invention is washable. In this regard, note particularly FIGS. 2, 3 and 5 where flexible polymeric bill element 32 is shown to define a plurality of openings 33 therethrough. Such openings not only improve flexibility of bill element 32, but likewise provide a means for escape or drainage of water through bill element 32 to facilitate drying and preclude prolonged entrapment of moisture or water thereat.

One further characteristic that may be achievable with a sun visor of the type described hereinbefore is reversibility. While the particular techniques utilized in fabrication of the sun visor according to the present invention may vary considerably, the reversibility characteristic is generally achievable when all of the structural elements are flexible, and thus bendable without danger of creasing or rupture. Consequently, the sun visor of the present invention may be turned inside-out such that inside covering material 24 of body section 10 becomes the outside covering material and the under covering material 36 of bill section 30 becomes the upper covering material. It is in this particular embodiment where color characteristics of the various covering materials can become important, not only for decorative affects, but also prolonging useful life of the product.

While the various materials alluded to above for use in the sun visor structure according to the present invention have been defined in a preferred fashion, obviously such are not limiting so long as the intended characteristics of the visor are maintained. Likewise, the particular arrangement for fabrication of the sun visor such as the stitching shown, is not critical to the structure of the present invention again so long as the functional requisites of the sun visor are maintained.

It will be understood, of course, that while the form of the invention herein shown and described constitutes a preferred embodiment of the invention, it is not intended to illustrate all possible form of the invention. It will also be understood that the words used are words of description rather than of limitation and that various changes may be made without departing from the spirit and scope of the invention herein disclosed.

What is claimed is:

1. An improved sun visor comprising a generally circular flexible body section for receipt about a human head, said body section having front, side and rear portions, said body section having a base material of polymeric foam along at least a major portion of the circumference of same and adjustment means located along at least one of said side and rear portions, said body section having an outer covering material and an inner covering material, said covering material being secured about said base material, and a flexible bill section secured to said body section along a lower edge of said front portion of same to form a generally convex curvature, said bill section being of a polymeric material inert as to water and including top and bottom covering materials secured thereabout, said bill section where secured to said lower edge of said body section being secured within said outer and inner covering materials of said body section so as to achieve reversibility where said inner covering material of said body section becomes the outer covering and said bottom covering material of said bill section becomes the top covering.

2. A sun visor as defined in claim 1 wherein the covering materials for said body section and said bill section are fabrics.

3. A sun visor as defined in claim 2 wherein fabrics of differing physical characteristics are employed.

4. A sun visor as defined in claim 1 wherein said adjustment means is an elastic strip and said strip is located along said rear portion of said body section.

5. A sun visor as defined in claim 1 wherein said polymeric bill section defines a plurality of openings therein so that water can escape therethrough.

6. A sun visor as defined in claim 1 further including stitching for securing said bill section within said outer and inner covering materials of said body section.

7. A sun visor as defined in claim 2 wherein said fabrics are terry-type fabrics.

8. A sun visor as defined in claim 1 wherein said front portion of said body section is higher than said side and rear portions.

9. An improved sun visor comprising a generally circular, flexible body section for receipt about a human head, said body section having front, side and rear portions, said body section having a flexible polymeric foam along at least a major portion of the circumference of same and an elastic strip along at least one of said side and rear portions, said body section having outer covering fabric and inner covering fabric secured about said foam and said elastic strip, and a flexible polymeric bill element secured to said body section within said outer and inner covering fabrics along a lower edge of said front portion to form a generally convex curvature thereacross, said bill element having an arcuate outer free edge and having top and bottom covering fabrics secured thereabout, said securement of said bill element to said body section permitting said visor to be reversed, all of said foam, elastic strip, bill element and covering fabrics being resistant to deterioration in water.

10. A sun visor as defined in claim 9 wherein said bill element defines a plurality of openings thereacross to facilitate drainage of water therethrough.

11. A sun visor as defined in claim 9 wherein said fabric coverings are absorbent as to liquids.

12. A sun visor as defined in claim 9 wherein said front portion of said body section is greater in height than said side and rear portions.

13. A sun visor as defined in claim 9 wherein said foam is an open cell foam.

* * * * *